US006312464B1

United States Patent
Navia

(10) Patent No.: US 6,312,464 B1
(45) Date of Patent: Nov. 6, 2001

(54) METHOD OF IMPLANTING A STENTLESS CARDIAC VALVE PROSTHESIS

(76) Inventor: José L. Navia, 2707 Cranlyn Rd., Shaker Heights, OH (US) 44122

( * ) Notice: Subject to any disclaimer, the term of this patent is extended or adjusted under 35 U.S.C. 154(b) by 0 days.

(21) Appl. No.: 09/301,101

(22) Filed: Apr. 28, 1999

(51) Int. Cl.$^7$ .................................................... A61F 2/24
(52) U.S. Cl. ........................................ 623/2.12; 128/898
(58) Field of Search .............................. 128/898; 623/2.1, 623/2.11, 2.12, 2.13, 2.14, 2.15, 2.16, 2.17, 2.18, 2.19

(56) References Cited

U.S. PATENT DOCUMENTS

| | | | |
|---|---|---|---|
| 3,548,418 | 12/1970 | Angell et al. | 3/1 |
| 3,656,185 | 4/1972 | Carpentier | 3/1 |
| 3,898,701 | 8/1975 | La Russa | 3/1.5 |
| 4,084,268 | 4/1978 | Ionescu et al. | 3/5 |
| 4,261,342 | 4/1981 | Duo | 128/1 R |
| 4,769,032 | 9/1988 | Steinberg | 623/2 |
| 4,790,844 | 12/1988 | Ovil | 623/2 |
| 4,960,424 | 10/1990 | Grooters | 623/2 |
| 5,037,434 | 8/1991 | Lane | 623/2 |
| 5,061,277 | 10/1991 | Carpentier et al. | 623/2 |
| 5,147,391 | 9/1992 | Lane | 623/2 |
| 5,156,621 | 10/1992 | Navia et al. | 623/2 |
| 5,336,258 | 8/1994 | Quintero et al. | 623/2 |
| 5,344,442 | 9/1994 | Deac | 623/2 |
| 5,352,240 | 10/1994 | Ross | 623/2 |
| 5,415,667 | 5/1995 | Frater | 623/2 |
| 5,480,424 | 1/1996 | Cox | 623/2 |
| 5,500,015 | 3/1996 | Deac | 623/2 |
| 5,554,184 | 9/1996 | Machiraju | 623/2 |
| 5,662,704 | 9/1997 | Gross | 623/2 |
| 5,713,950 | 2/1998 | Cox | 623/2 |
| 5,713,953 | 2/1998 | Vallana et al. | 623/2 |
| 5,716,417 | 2/1998 | Girard et al. | 623/900 |
| 5,733,331 | 3/1998 | Peredo | 623/2 |
| 5,824,060 | 10/1998 | Christie et al. | 623/2 |
| 5,855,601 | 1/1999 | Bessler et al. | 623/2 |
| 5,855,602 | 1/1999 | Angell | 623/2 |

FOREIGN PATENT DOCUMENTS 2 355 492    11/1976   (FR) .

OTHER PUBLICATIONS

Athanasuleas et al. "The autologous rectus sheath cardiac valve" Journal of Thoracic and Cardiovascular Surgery, 65(1):118–123 (1973).

Choh, "Preservation of Anterior and Posterior Leaflet in Mitral Valve Replacement with a Tilting–Disc Valve" Ann Thorac Surg 64:271–3 (1997).

Deac et al., "New Evolution in Mitral Physiology and Surgery: Mitral Stentless Pericardial Valve" Ann Thorac Surg 60:S433–8 (1995).

Lillehei et al., "Mitral Valve Replacement with Preservation of Papillary Muscles and Chordae Tendineae" J. Thoracic and Cardiovas. Surg. 47(4):532–543 (Apr. 1964).

Navia et al., "Low profile bioprosthesis for cardiac valve replacement:hydraulic and hemodynamic studies" Medical Instrumentation 16(1):57–59 (Jan./Feb. 1982).

(List continued on next page.)

*Primary Examiner*—David J. Isabella
(74) *Attorney, Agent, or Firm*—Heller Ehrman White & McAuliffe LLP

(57) ABSTRACT

A method of implanting a valve prosthesis in an atrio-ventricular valve of a patient's heart generally comprising securing a distal end of the valve prosthesis to the leaflets of the atrio-ventricular valve, and securing a proximal end of the valve prosthesis to the annulus of the atrio-ventricular valve, so that the chordae tendineae and the continuity between the papillary muscle and the valve annulus of the atrio-ventricular valve is preserved. Depending on the etiology of the valve disease, the method of the invention may comprises implanting the valve prosthesis in an intact atrio-ventricular valve, or alternatively, in a resected atrio-ventricular valve.

15 Claims, 9 Drawing Sheets

OTHER PUBLICATIONS

Okita et al., "Mitral valve replacement with maintenance of mitral annulopapillary muscle continuity in patients with mitral stenosis" J. Thoracic and Cardiovac. Surg. 108(1):42–51 (Jul. 1994).

Osvaldo et al., "Surgical Technique of Implanting the Stentless Porcine Mitral Valve" Ann. Thorac. Surg. 60:S439–42 (1995).

O'Brien, "Heterograft aortic valves for human use . . . *Valve bank, techniques of measurement and implanation*" J. Thorac and Cardiovas. Surg. 53(3):392–7 (Mar. 1967).

Sintek et al., "Mitral Valve Replacement: Technique to Preserve the Subvalvular Apparatus" Ann. Thorac. Surg. 59:1027–9 (1995).

Yacoub et al., "A new technique for replacement of the mitral valve by a semilunar valve homograft" J. Thorac. and Cardiovas. Surg. 58(6):859–869 (Dec. 1969).

Yun et al., "Mitral Valve Replacement" Two.Adult Cardiac Surgery, 34:329–341.

METHOD OF IMPLANTING A STENTLESS CARDIAC VALVE PROSTHESIS

BACKGROUND OF THE INVENTION

This invention generally relates to the field of cardiac valve replacement, and more particularly to a method of implanting a stentless valve prosthesis in an atrio-ventricular valve of a patient's heart.

A human heart includes two atrio-ventricular valves, namely the tricuspid valve between the right atrium and ventricle, and the mitral or bicuspid valve between the left atrium and ventricle. The atrio-ventricular valves are one-way valves, permitting blood flow from the atrium to the ventricle. During the cardiac cycle, the valves function as part of a unit composed of multiple interrelated parts, including the ventricular and atrial walls, the valve leaflets, the fibrous skeleton of the heart at the atrio-ventricular ring, and the subvalvular apparatus. The subvalvular apparatus includes the papillary muscle within the ventricle, and the chordae tendineae which connect the papillary muscle to the valve leaflets.

Surgical procedures for repairing or replacing diseased atrio-ventricular valves are well known. Reparative techniques are typically not feasible in cases involving extensive fibrosis, leaflet calcification, or massive chordal rupture, leaving valve replacement as the only surgical option. The valve may be replaced either with a mechanical or biological valve prosthesis. Biological valve prostheses are formed of tissue, and include allografts, e.g., aortic valves from cadavers, and xenografts formed of animal tissue. The valves may include a metal or plastic support, typically called a stent, or may be stentless.

Mitral valve replacement generally involves either conventional replacement methods or chordal-sparing replacement methods, as described in K. L. Yun et al., Mitral Valve Replacement, Chpt. 2, Adult Cardiac Surgery, in Mastery of Cardiothoracic Surgery, L. R. Kaiser et al Eds., 329–341 (1988), incorporated herein by reference in its entirety. In conventional replacement, the mitral leaflets and subvalvular apparatus are completely removed before the prosthesis is implanted. In contrast, in chordal-sparing replacement, at least the choral attachments to the posterior leaflet of the mitral valve are preserved. Maintaining the continuity of the mitral annulus and papillary muscle by preserving the subvalvular apparatus during mitral valve replacement has been suggested as an important feature in maintaining normal left ventricular function, as described by Lillehei et al, J. Thoracic and Cardiovas. Surg., Vol. 47, No. 4, 532–543 (1964), incorporated herein by reference in its entirety. Following implantation of a stented valve prosthesis, one difficulty has been reduced heart function, including limitation of the mitral flow, higher cardiac output due to a size mismatch between the prosthesis and native valve, and limitation of the physiologic contraction of the posterior wall of the left ventricle surrounding the mitral annulus during systole due to the rigid structure of some valve prostheses.

It would be a significant advance to provide a method of implanting a stentless valve prosthesis in an atrio-ventricular valve which maintains normal heart function.

SUMMARY OF THE INVENTION

This invention is directed to a method of implanting a valve prosthesis in an atrio-ventricular valve of a patient's heart in which a section of the valve prosthesis is secured to a leaflet of the atrio-ventricular valve, so that the patient's atrio-ventricular valve supports the implanted valve prosthesis. The method of the invention preserves the chordae tendineae of the atrio-ventricular valve and thus the continuity between the papillary muscle and the valve annulus of the native atrio-ventricular valve.

The method of the invention generally comprises securing a distal end of the valve prosthesis to the leaflets of the atrio-ventricular valve, and securing a proximal end of the valve prosthesis to the annulus of the atrio-ventricular valve. The term distal should be understood to mean the downstream end of the implanted valve prosthesis, and the term proximal should be understood to mean the upstream end of the implanted valve prosthesis. In a presently preferred embodiment, the atrio-ventricular valve is the mitral valve, although the method may also be used in implanting a valve prosthesis in the tricuspid valve.

The valve prosthesis is preferably a stentless prosthesis. In one embodiment, the valve prosthesis is a biological prosthesis such as a porcine aortic valve. A suitable stentless biological valve prosthesis is described in U.S. Pat. No. 5,156,621 (Navia et al.), incorporated herein by reference in its entirety, generally comprising an aortic valve having a suture ring, anchoring skirts at the commissures of the valve, and an outer polyester coating. A stentless valve prosthesis secured to the native valve annulus and leaflets according to the method of the invention reduces tissue stress as the flexible valve prosthesis adapts and conforms to the native valve, so that durability and resistance to wear and calcification is improved. Additionally, a large orifice is provided having a circumference sized to correspond to the size of the patient's native valve, with a resulting unrestricted flow and corresponding high cardiac output during exercise and low opening pressure without a gradient across the valve, and rapid opening and closing at all pressure ranges without regurgitant flow or obstruction of the ventricular outflow tract.

Depending on the etiology of the valve disease, the method of the invention may comprises implanting the valve prosthesis in an intact atrio-ventricular valve, or alternatively, in a resected atrio-ventricular valve. In one embodiment, the valve prosthesis is implanted in an intact atrio-ventricular valve, as for example, in the case of leaflet prolapse, chordal rupture in which chordal repair is not indicated, or mitral regurgitation due to annular dilatation. In another embodiment, a portion of the atrio-ventricular valve leaflets are first removed prior to implantation of the valve prosthesis, as for example, in the case of rheumatic fever. Sufficient amounts of the diseased valve are resected to allow for implantation of an adequate sized valve prosthesis, while not sacrificing valve annulus-papillary muscle continuity. A significant area of the atrio-ventricular valve leaflets remain for attachment and support of the distal end of the valve prosthesis. About 30% to about 70%, preferably about 40% to about 60%, and most preferably at least about 50% of the atrio-ventricular valve remains after the resection and provides a surface for attachment to the valve prosthesis. Unlike methods in which a significant portion of the atrio-ventricular valve leaflet is resected and the remaining portion of the leaflet is resuspended to the annulus, in the method of the invention a portion of the valve leaflet is preserved which is sufficient to support the valve prosthesis without rupturing. In one embodiment, three portions of the valve leaflets of the atrioventricular valve are left for attachment to the commissural portions of a valve prosthesis which has three commissural portions.

The method of the invention provides for implantation of a valve prosthesis, in which the prosthesis is attached to valve leaflets of the native atrio-ventricular valve, without impairing heart function. The valve annulus-papillary muscle continuity is maintained, and the ventricular geometry, mechanics and performance is preserved. Moreover, the method of the invention avoids the use of artificial chordae or special echocardiographic measurements, thus simplifying the procedure and reducing the surgeon skill level required.

These and other advantages of the invention will become more apparent from the following detailed description of the invention and the accompanying exemplary drawings.

BRIEF DESCRIPTION OF THE DRAWINGS

FIG. 3b is a top view of the stentless valve prosthesis shown in FIG. 3a.

FIG. 3c is a side view of the stentless valve prosthesis shown in FIG. 3a.

FIG. 3d is a bottom view of the stentless valve prosthesis shown in FIG. 3a.

DETAILED DESCRIPTION OF THE INVENTION

Figure 1:
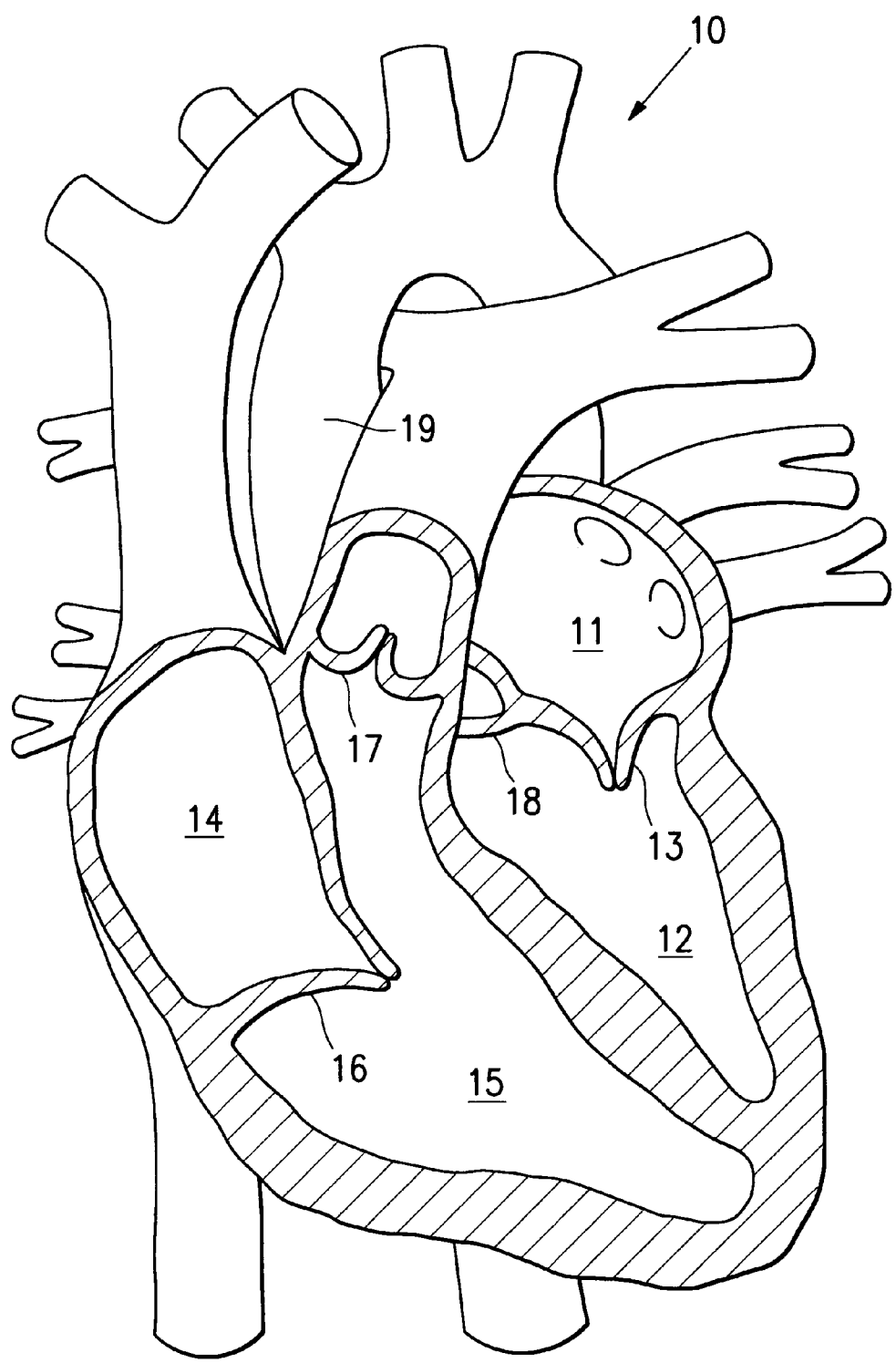
FIG. 1 is a longitudinal cross-sectional view of a patient's heart.
Figure 2:
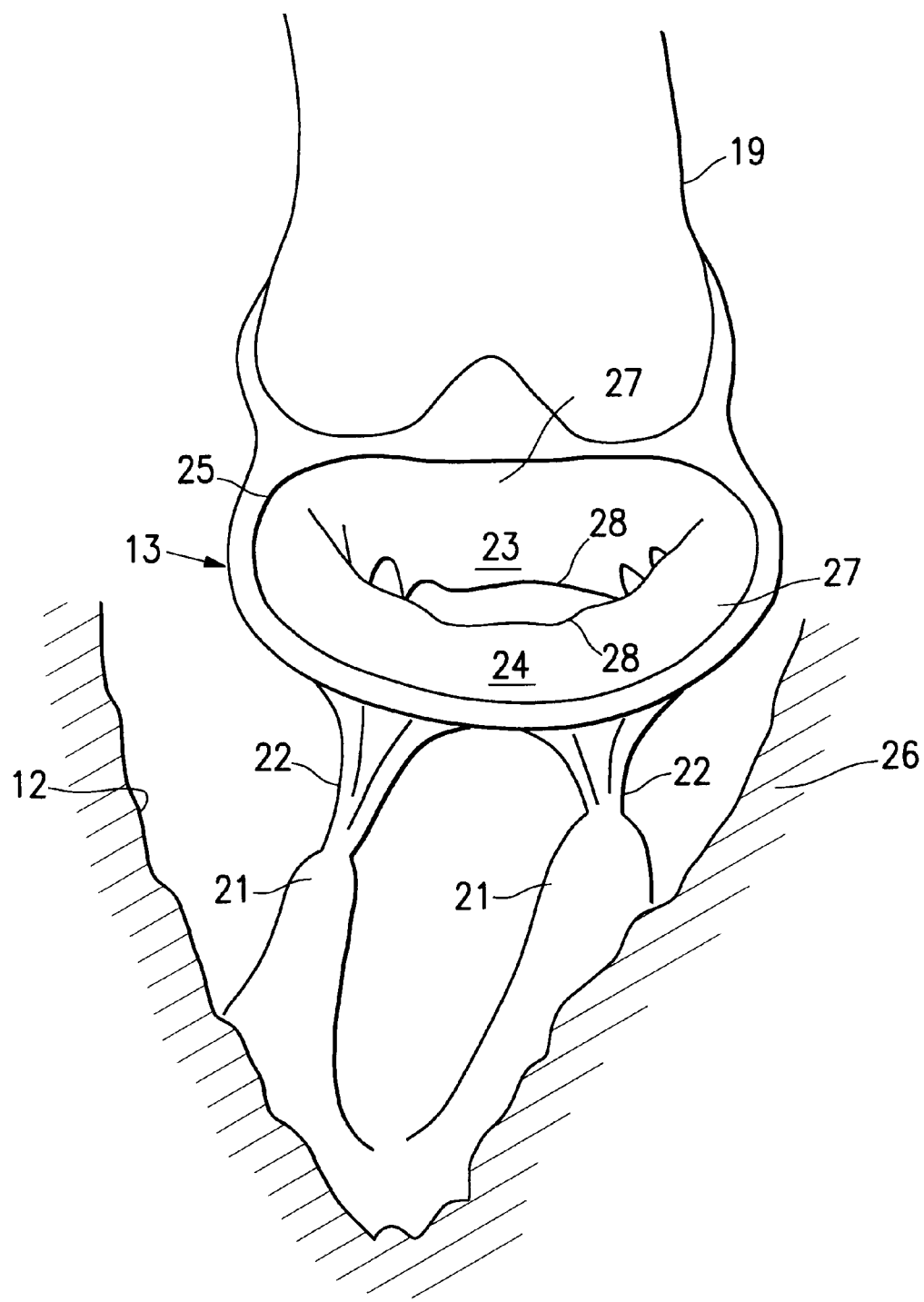
FIG. 2 is an elevational view of a mitral valve and left ventricle.
Figure 3A:
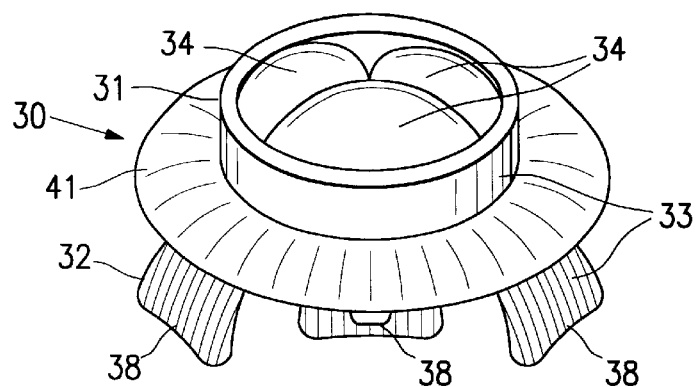
FIG. 3a is an elevational view of a stentless valve prosthesis suitable for use in the method of the invention.
Figure 3B:
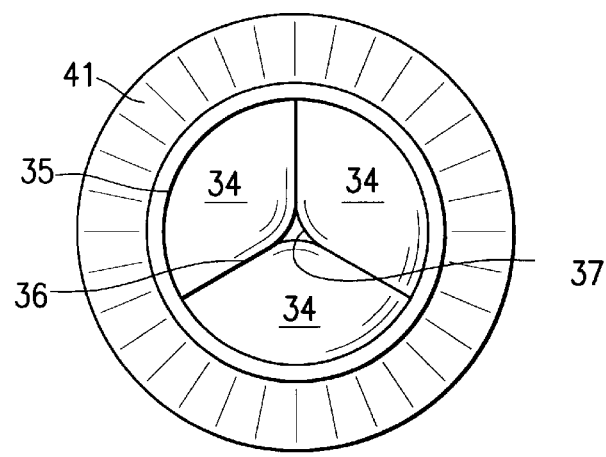
Figure 3C:
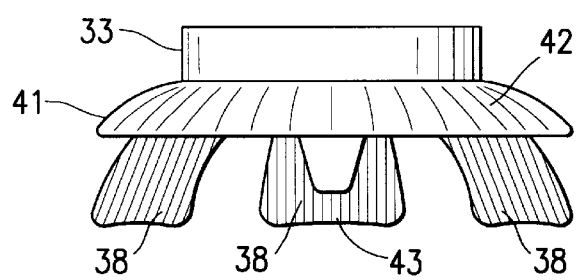
Figure 3D:
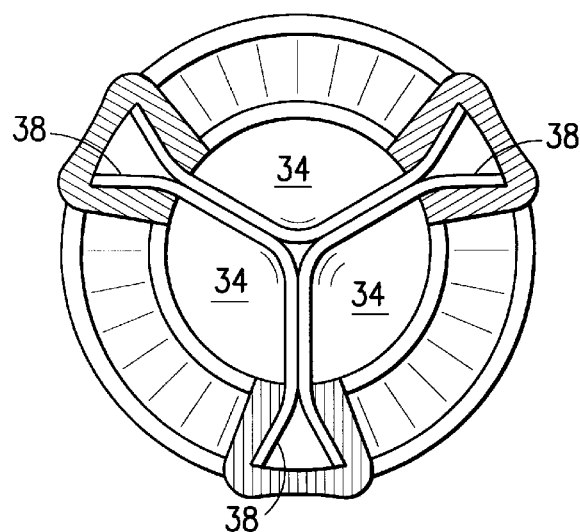

FIG. 1 illustrates a simplified cross-sectional view of a patient's heart 10, including a left atrium 11, left ventricle 12, mitral valve, 13, right atrium 14, right ventricle 15, tricuspid valve 16, pulmonary valve 17, aortic valve 18, and aorta 19. FIG. 2 shows a cross-sectional view of a patient's left ventricle 12, illustrating an elevational view of mitral valve 13, papillary muscles 21 and chordae tendineae 22, and aorta 19 adjacent the mitral valve. The mitral valve has an anterior leaflet 23 and a posterior leaflet 24 connected to the papillary muscles by the chordae tendineae 22, and a valve annulus 25 connected to the heart wall 26. The leaflets of the mitral valve have a superior edge 27 adjacent to the valve annulus, and an inferior edge, also known as a free edge, 28 adjacent to a connection of the chordae tendineae with the mitral valve leaflet.

In the method of the invention, a stentless valve prosthesis is secured to a leaflet and a valve annulus of an atrioventricular valve. FIGS. 3a–3d illustrate a valve prosthesis 30 suitable for use in the invention. The valve prosthesis 30 generally includes a proximal end 31, a distal end 32, a tubular body 33, a plurality of leaflets 34 secured to the tubular body. Each leaflet 34 has a secured edge 35 around an outer circumference of the valve prosthesis, and a free edge 36 extending within a central area of the valve prosthesis. The leaflets define a reversibly closeable passageway 37 through the valve prosthesis, illustrated in the closed configuration in FIGS. 3a–3d. In the embodiment illustrated in FIGS. 3a–3d, the valve prosthesis has three leaflets, as for example in an aortic valve, and three corresponding commissural portions 38 at the intersection of the secured edges of adjacent leaflets. Notches are cut out of the tubular body of the valve prosthesis between each commissural portion. A suture ring 41 is on a proximal section of the prosthesis. The suture ring is preferably DACRON, and is located distal to the proximal end of the valve prosthesis. Alternatively, the suture ring 41 may be located at the proximal edge of the valve prosthesis, as shown in U.S. Pat. No. 5,156,621, incorporated by reference herein above. An outer layer of a polymeric material 42 such a polyester, such as DACRON, covers the outer surface of the valve prosthesis and suture ring. In the valve prosthesis illustrated in FIGS. 3a–3d, a projection 43 of polymeric material extends distally of the distal end of the tubular body 33. In a presently preferred method of the invention the valve bioprosthesis is a stentless aortic porcine valve. However, a variety of suitable valve prostheses may be used.

Figure 4:
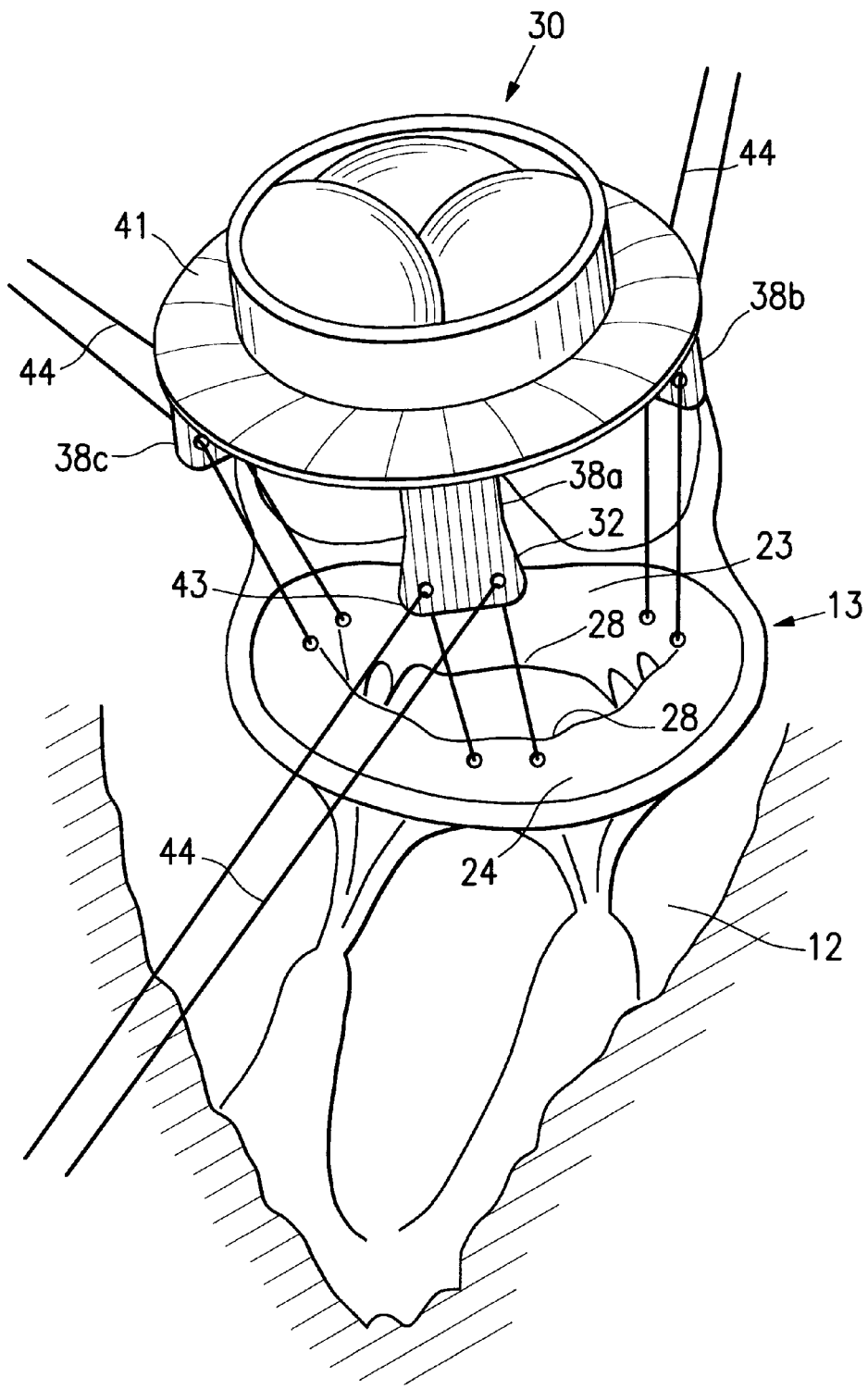
FIG. 4 is an elevational view of a stentless valve prosthesis being sutured to valve leaflets of an intact mitral valve, according to a method which embodies features of the invention.
Figure 5:
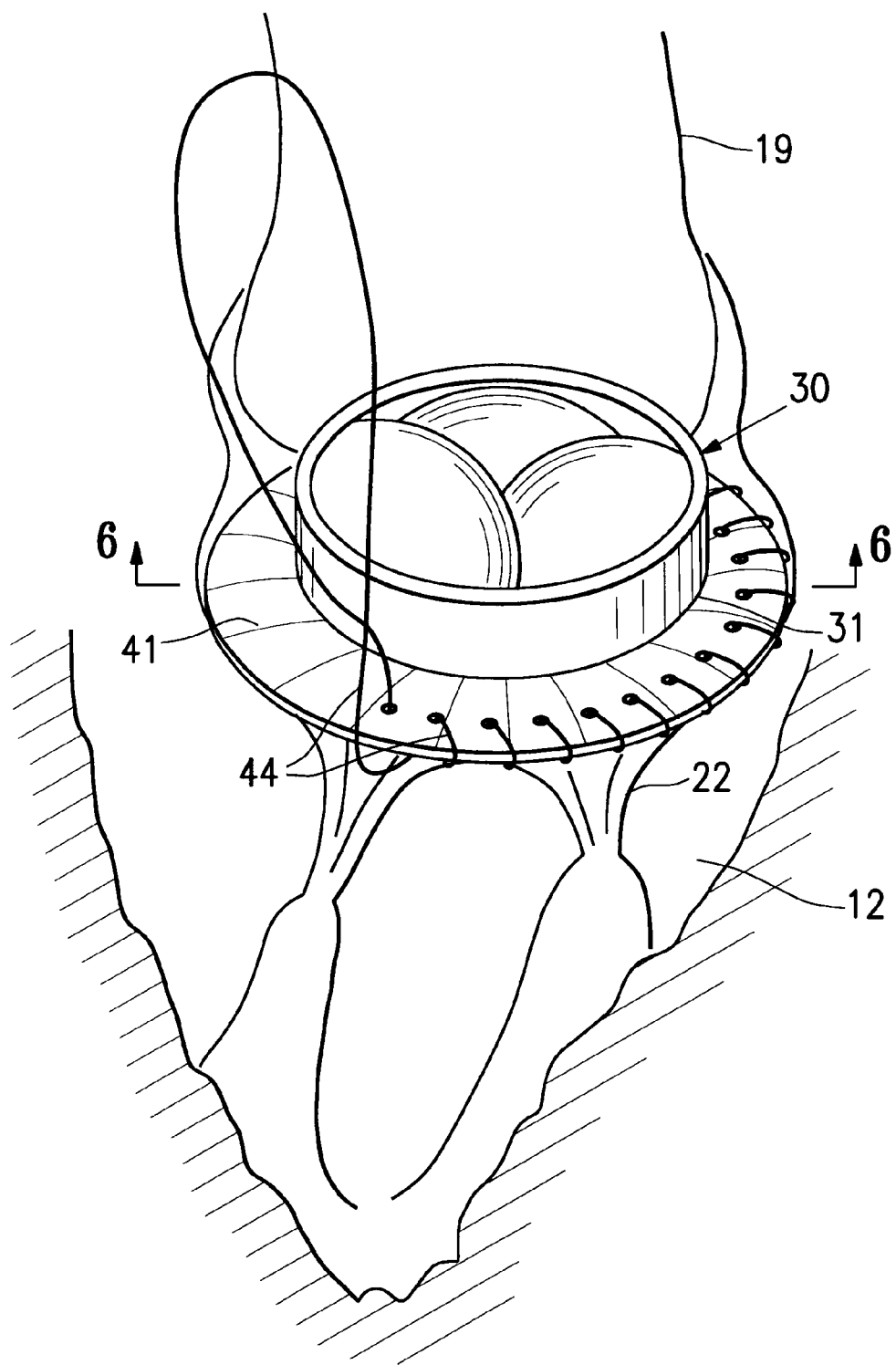
FIG. 5 is an elevational view of a stentless valve prosthesis implanted in an intact mitral valve with the prosthesis ring being sutured to the mitral annulus, according to a method which embodies features of the invention.

FIGS. 4 and 5 illustrate the implantation of a stentless valve prosthesis 30 in a mitral valve 13 of a patient according to one embodiment of the method of the invention. The distal end 32 of the stentless valve prosthesis, at the distal end of each commissural portion 38, is secured to the leaflets 23, 24 of the intact mitral valve 13 with sutures 44. In the embodiment illustrated in FIG. 4, projection 43 of polymeric material at the distal end of the commissure is sutured directly to the mitral valve leaflets 23, 24. Alternatively, the tubular body 33 at a distal section of the commissural portion 38 proximal to the projection 43 may be sutured to the mitral valve leaflets. In the embodiment illustrated in FIG. 4, a first commissural portion 38a is sutured to a middle portion of the posterior leaflet 24 of the mitral valve, a second commissural portion 38b is sutured to a first lateral portion at one end of the anterior leaflet 23, and a third commissural portion is sutured to a second lateral portion at an opposite end of the anterior leaflet. In the embodiment illustrated in FIG. 4, the distal end of the valve prosthesis is sutured to an inferior portion of the mitral valve adjacent to the inferior edge 27, which is adjacent to a connection of the chordae tendineae with the mitral valve leaflet. In a presently preferred embodiment, the sutures 44 used to secure the distal section of the outer surface of each commissure to the leaflet of the mitral valve comprise a 4-O polyester suture, with or without TEFLON pledgets.

Figure 6:
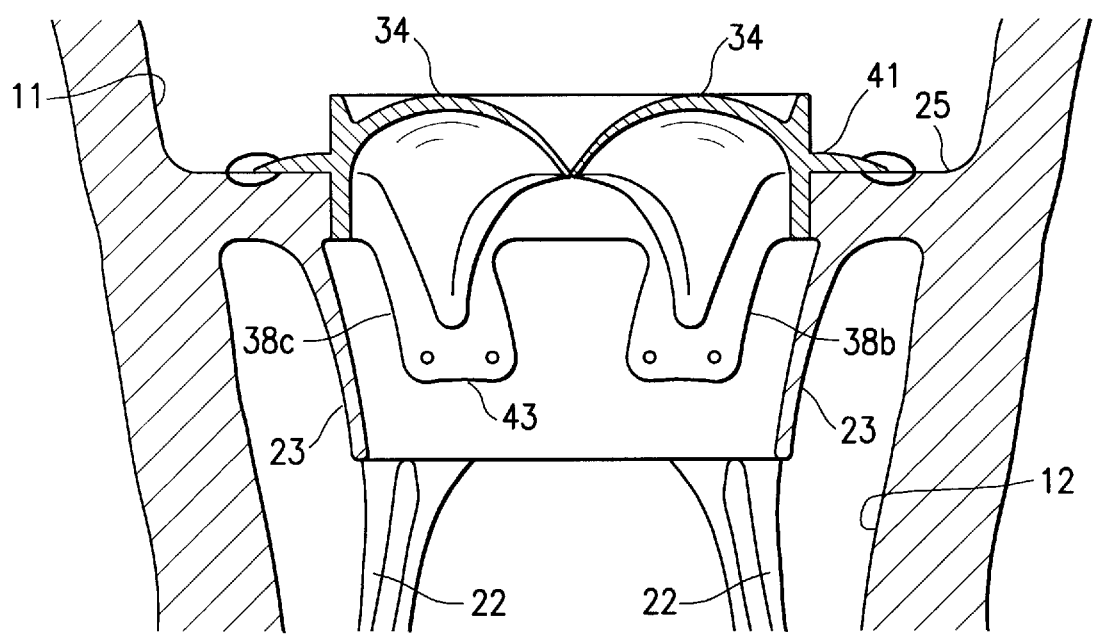
FIG. 6 is a longitudinal cross-sectional view of the implanted valve prosthesis shown in FIG. 5.

The proximal end 31 of the valve prosthesis is sutured to the mitral valve annulus, as illustrated in FIG. 5. In a presently preferred embodiment, suture ring 41 is secured to the mitral annulus with interrupted 2-O polyester sutures 44 reinforced with TEFLON pledgets, placed in a noneverting fashion from the ventricular to the atrial side, or with a running suture technique using 4-O PROLENE. FIG. 6 illustrates a longitudinal cross sectional view of the implanted stentless valve prosthesis shown in FIG. 5, taken along lines 6—6, sutured to the mitral valve annulus 25 and leaflets 23, 24. In the cross sectional view shown in FIG. 6, only the anterior leaflet 23, having the second and third commissural portions sutured thereto, is visible. As discussed above, the method of the invention may be used in other cardiac valves such as the tricuspid valve. Thus, in the case of, for example, severe tricuspid regurgitation due to leaflet prolapse, severe annular dilatation or chordal rupture, the valve prosthesis may be implanted according to the method of the invention in an intact tricuspid valve, as described above. The distal end of each commissural portion of the stentless valve prosthesis is secured to the inferior portion of the three leaflets of the intact tricuspid valve, i.e., the anterior, posterior and septal leaflets, with a 4-O polyester suture with or without TEFLON pledgets. The valve prosthesis ring is secured to the native tricuspid annulus with interrupted 2-O polyester sutures reinforced with TEFLON pledgets or by using 4-O PROLENE with a running suture technique.

Figure 7A:
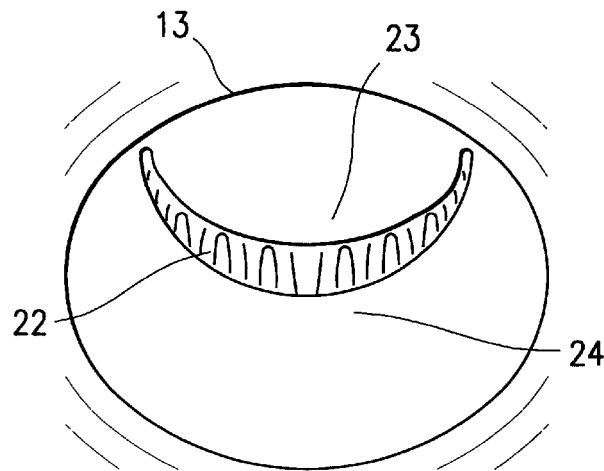
FIG. 7a is a top view of an intact mitral valve.
Figure 7B:
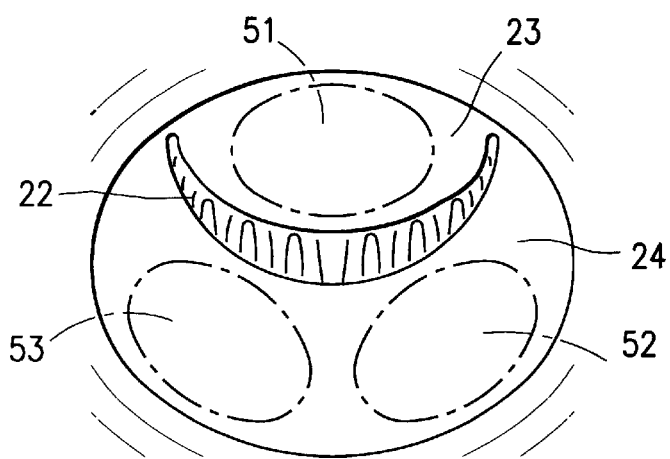
FIGS. 7b and 7c are top and bottom views, respectively, of the resected mitral valve having a portion of the valve leaflets removed according to a method which embodies features of the invention.
Figure 7C:
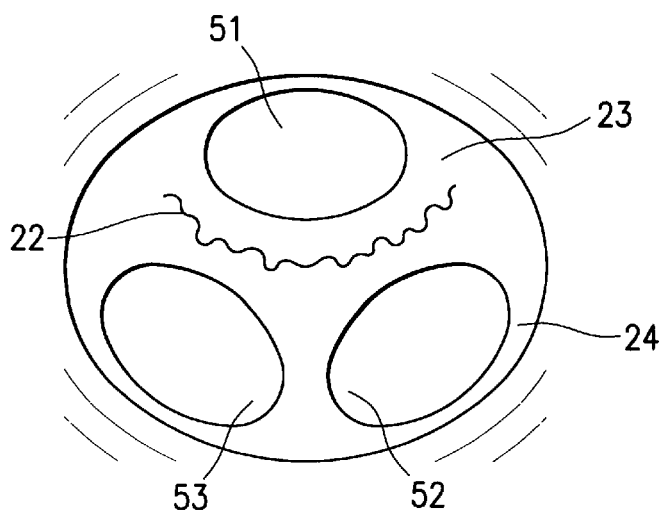
Figure 8:
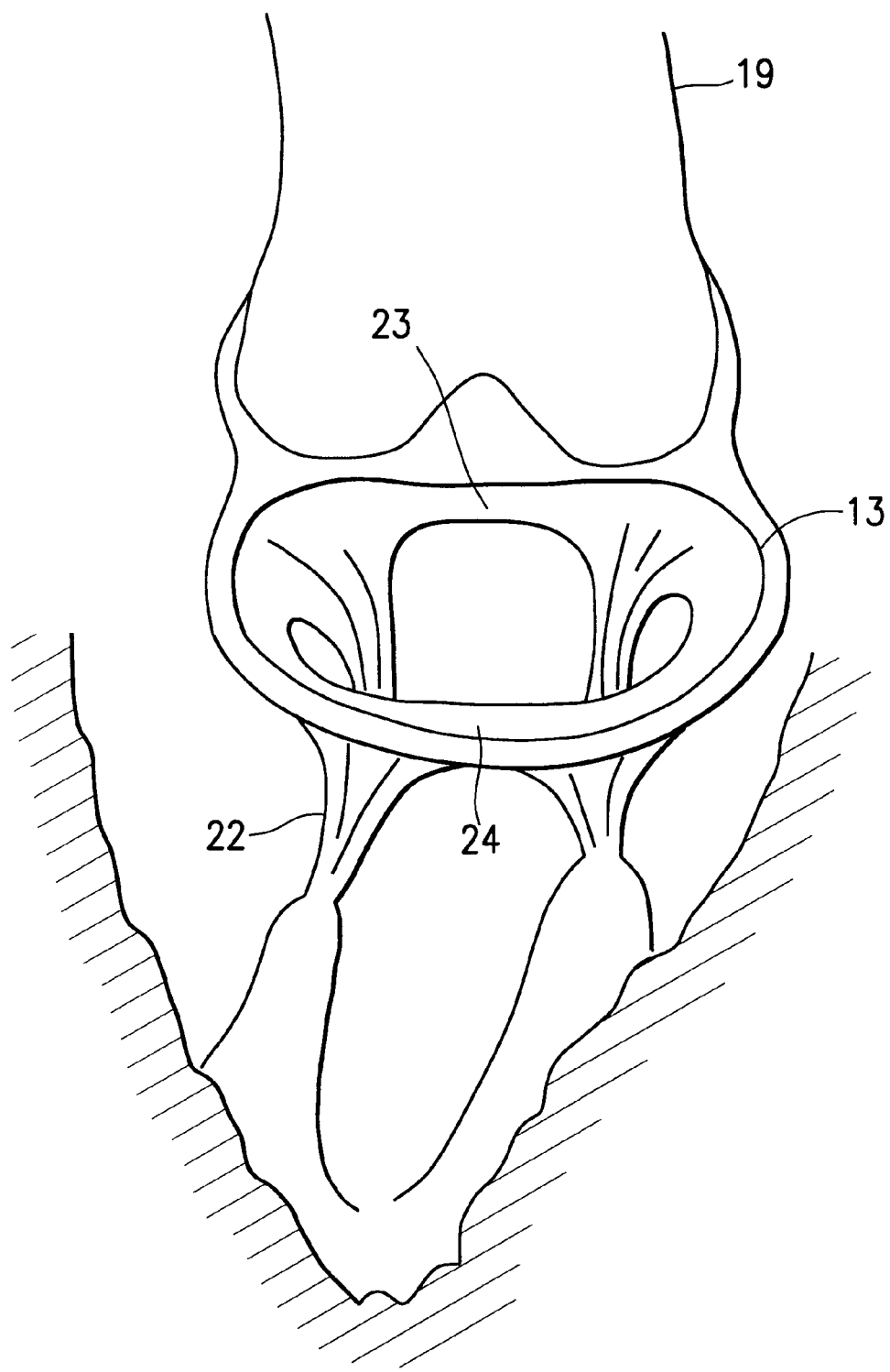
FIG. 8 is an elevational view of a resected mitral valve and left ventricle of a patient, after a portion of the valve leaflets are removed according to a method which embodies features of the invention.
Figure 9:
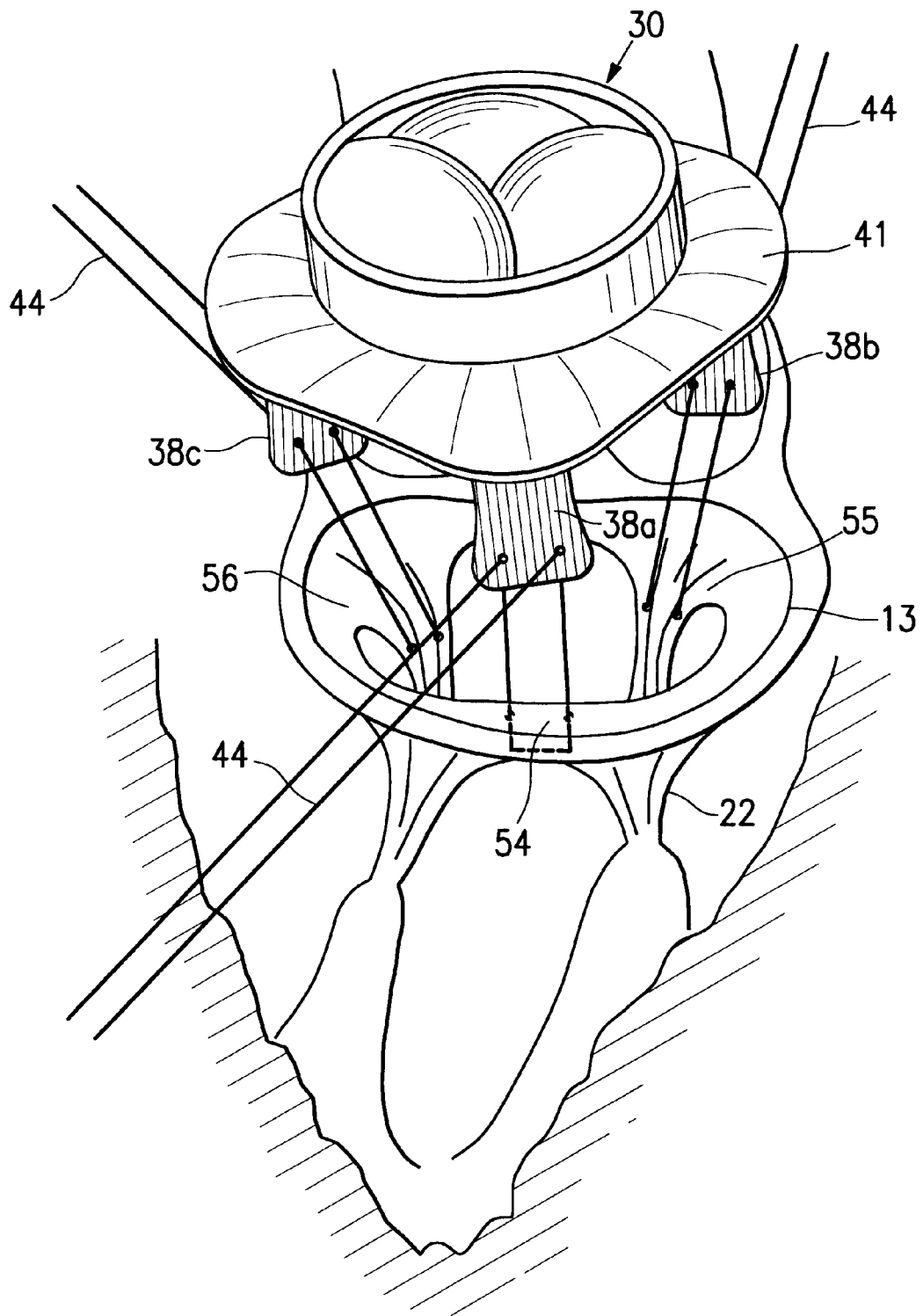
FIG. 9 is an elevational view of a stentless valve prosthesis during suturing of the valve prosthesis to valve leaflets of a resected mitral valve according to a method which embodies features of the invention.

In another embodiment of the method of the invention, a portion of the mitral valve leaflets is removed and the distal section of the valve prosthesis is secured to remaining portions of the mitral valve leaflets. FIG. 7a illustrates a top view of an intact mitral valve, showing the anterior leaflet 23, the posterior leaflet 24, and the chordae tendineae 22 attached to the anterior leaflet. In one embodiment, a middle portion 51 of the mitral valve anterior leaflet is resected, and a first lateral portion 52 and a second lateral portion 53 of the mitral valve posterior leaflet is resected, as illustrated in FIGS. 7b and 7c, illustrating a top and bottom view, respectively, of resected valve leaflets. In FIGS. 7b and 7c, the portion of the leaflet corresponding to the first lateral portion 52 is also known as the antero-lateral portion, and the second lateral portion 53 is also known as the posterior-medial portion. The portion of the mitral valve leaflet which is removed is displaced from the connection of the chordae tendineae and the mitral valve leaflet, so that at least some of the chordae tendineae 22 are left connected to the mitral valve leaflet 23, 24 after the resection of the mitral valve leaflet. Thus, some of the chordae tendineae attached to the leaflet 23, 24, and particularly some of the chordal attachments to the anterior leaflet, may be disconnected from the leaflet as a result of the removal of a portion of the leaflets, but without interfering with valve annulus-papillary muscle continuity. Less than about 70% to about 30%, preferably less than about 60% to about 40%, and most preferably less than about 50% to about 40% of the total area of the mitral valve leaflet tissue is removed, so that a sufficient amount of leaflet remains for attachment to, and support of, the valve prosthesis. FIG. 8 illustrates the mitral valve with a middle portion 51 of the anterior leaflet 23 and first lateral portion 52 and second lateral portion 53 of the posterior leaflet removed. FIG. 9 illustrates the implantation of a stentless valve prosthesis 30 in the resected mitral valve 13. The first commissural portion 38a is sutured to a middle portion 54 of the posterior leaflet, a second commissural portion 38b is sutured to a first lateral portion 55 of the anterior leaflet, and third commissural portion 38c is sutured to a second lateral portion 56 of the anterior leaflet. Typically, the resected leaflet portions are each about 10 to about 15 millimeters long, and about 5 to about 10 millimeters wide, and about 8 to about 10 square millimeters in area. The remaining valve leaflet portions do not interfere with the functioning of the implanted valve prosthesis. The middle portion 54 of the posterior leaflet is about 10 to about 15 square millimeters in area. The first lateral portion 55 of the anterior leaflet is about 8 to about 10 square millimeters in area, and the second lateral portion 56 of the anterior leaflet is about 8 to about 10 square millimeters in area. As discussed above, the distal end of each commissural portion is sutured to an inferior portion of the mitral valve adjacent a location on the mitral valve leaflet where the chordae tendineae connect to the mitral valve leaflet. The suturing of the proximal end of the valve prosthesis to the mitral valve annulus is as discussed above. The valve prosthesis may implanted in a tricuspid valve in which a portion of a tricuspid valve leaflet is removed, as for example in the case of tricuspid stenosis and tricuspid endocarditis. At least a middle portion of each of the three leaflets of the native tricuspid valve remains after one or more lateral portions on either side of the middle portion are removed, for securing to the commissural portions of the valve prosthesis, as discussed above.

To the extent not previously described herein, the surgical implantation may be performed using surgical procedures well known in the art, including initiating cardiopulmonary bypass with an arterial cannula, cross-clamping the aorta, and arresting the heart with cold crystalloid cardioplegia or blood. Similarly, the biological valve prosthesis may be prepared for implanting, as is conventionally known. For example, xenograft valves may be treated with an agent such as glutaraldehyde, using conventional procedures, to fix and sterilize the valve tissue, and reduce its antigenicity.

While the present invention has been described herein in terms of certain preferred embodiments, those skilled in the art will recognize that modifications and improvements may be made without departing form the scope of the invention.

What is claimed is:

1. A method of implanting a valve prosthesis in an atrio-ventricular valve of a patient's heart, comprising:
   a) providing a stentless valve prosthesis having a proximal end and a distal end;
   b) securing a distal section of the valve prosthesis to a leaflet of the atrio-ventricular valve; and
   c) securing a proximal section of the valve prosthesis to an annulus of the atrio-ventricular valve.

2. The method of claim 1 wherein the valve prosthesis comprises a tubular body having a passageway therethrough, a plurality of leaflets within the tubular body and secured thereto, each leaflet having a secured edge and a free edge, and a plurality of commissural portions at the intersection of the secured edges of adjacent leaflets, and wherein securing the distal section of the valve prosthesis to the leaflets of the atrio-ventricular valve comprises suturing the commissural portions to the leaflets of the atrio-ventricular valve.

3. The method of claim 1 wherein the atrio-ventricular valve comprises a bicuspid valve having an anterior leaflet and a posterior leaflet, and securing the distal section of the valve prosthesis to the leaflets of the bicuspid valve comprises suturing a first commissural portion of the valve prosthesis to the posterior leaflet, and suturing at least a second commissural portion of the valve prosthesis to the anterior leaflet.

4. The method of claim 3 wherein the valve prosthesis comprises a bioprosthesis having three leaflets and three commissural portions, and further including suturing a third commissural portion of the valve prosthesis to the anterior leaflet.

5. The method of claim 4 wherein the first commissural portion is sutured to a middle portion of the posterior leaflet, the second commissural portion is sutured to a first lateral portion of the anterior leaflet, and the third commissural portion is sutured to a second lateral portion of the anterior leaflet.

6. The method of claim 2 wherein the valve prosthesis has an outer layer of a polymeric material on at least a portion of an outer surface of the tubular body, and the commissural portions include a projection of the polymeric material extending beyond a distal end of the tubular body, and wherein suturing the commissural portions to the leaflets comprises suturing the projections of polymeric material to the leaflets.

7. The method of claim 1 wherein the leaflets of the atrio-ventricular valve have a superior edge adjacent the valve annulus and an inferior edge adjacent a connection of chordae tendineae of the atrio-ventricular valve with the atrio-ventricular valve leaflet, and wherein securing the distal section of the valve prosthesis to the atrio-ventricular valve leaflets comprises suturing the distal end of the valve prosthesis to an inferior portion of the atrio-ventricular valve leaflet adjacent the inferior edge of the leaflets.

8. The method of claim 1 including removing a portion of the atrio-ventricular valve leaflets, and securing the distal section of the valve prosthesis to a remaining portion of the atrio-ventricular valve leaflets.

9. The method of claim 8 wherein the atrio-ventricular valve is a bicuspid valve having an anterior leaflet and a posterior leaflet, and including removing a middle portion of the anterior leaflet and a first lateral portion and a second lateral portion of the posterior leaflet.

10. The method of claim 9 wherein the valve prosthesis comprises a bioprosthesis having three leaflets and three commissural portions, and including suturing a first commissural portion to a middle portion of the posterior leaflet, a second commissural portion to a first lateral portion of the anterior leaflet, and a third commissural portion to a second lateral portion of the anterior leaflet.

11. The method of claim 8 wherein the atrio-ventricular valve leaflets are attached to papillary muscles by chordae tendineae of the patient's heart, and wherein removing a portion of the leaflet includes removing a portion of the leaflet displaced from a connection of the chordae tendineae with the leaflet of atrio-ventricular valve so that the leaflet remains attached to the papillary muscle.

12. The method of claim 11 wherein less than about 30% to about 70% of a total area of the leaflet is removed.

13. The method of claim 11 wherein less than about 40% to about 50% of a total area of the leaflet is removed.

14. The method of claim 1 wherein the valve prosthesis has a suture ring on the proximal section thereof, and wherein securing the proximal section of the valve prosthesis to the annulus comprises suturing the suture ring to the annulus, and wherein the distal section of the valve prosthesis secured to the atrio-ventricular valve is distal to the suture ring.

15. The method of claim 8 wherein the atrio-ventricular valve is a tricuspid valve having three leaflets, and including removing a lateral portion of at least one of the leaflets of the tricuspid valve.

* * * * *